United States Patent

Topholm et al.

(10) Patent No.: US 7,931,027 B2
(45) Date of Patent: Apr. 26, 2011

(54) EARPLUG WITH ENGAGEMENT MEANS

(75) Inventors: Jan Topholm, Holte (DK); Casper Hojstad Hansen, Horsholm (DK)

(73) Assignee: WIDEX A/S, Varlose (DK)

( * ) Notice: Subject to any disclaimer, the term of this patent is extended or adjusted under 35 U.S.C. 154(b) by 136 days.

(21) Appl. No.: 11/872,135

(22) Filed: Oct. 15, 2007

(65) Prior Publication Data

US 2009/0095307 A1    Apr. 16, 2009

(51) Int. Cl.
*A61F 11/00* (2006.01)
*H04R 25/00* (2006.01)
*A61B 7/02* (2006.01)

(52) U.S. Cl. ........ 128/864; 128/866; 381/328; 181/129; 181/135

(58) Field of Classification Search .................. 128/865, 128/864, 866; 181/135, 129, 130; 381/328, 381/322, 324; 607/55
See application file for complete search history.

(56) References Cited

U.S. PATENT DOCUMENTS

| | | |
|---|---|---|
| 4,607,720 A | 8/1986 | Hardt |
| 4,880,076 A | 11/1989 | Ahlberg et al. |
| 5,163,912 A * | 11/1992 | Gay et al. ................. 604/165.02 |
| 5,742,692 A | 4/1998 | Garcia et al. |
| 2002/0096391 A1 | 7/2002 | Smith et al. |
| 2003/0002700 A1 | 1/2003 | Frentz et al. |
| 2006/0045297 A1 * | 3/2006 | Haussmann ................. 381/322 |

FOREIGN PATENT DOCUMENTS

| | | |
|---|---|---|
| DE | 102006004033 A1 | 8/2007 |
| WO | 9907182 A2 | 2/1999 |
| WO | 2005062670 A2 | 7/2005 |
| WO | 2006026988 A1 | 3/2006 |
| WO | 2006094502 A1 | 9/2006 |
| WO | WO 2006094502 A1 * | 9/2006 |
| WO | 2007006302 A1 | 1/2007 |
| WO | WO 2007006302 A1 * | 1/2007 |

* cited by examiner

*Primary Examiner* — Patricia M Bianco
*Assistant Examiner* — Ophelia Hawthorne
(74) *Attorney, Agent, or Firm* — Sughrue Mion, PLLC

(57) ABSTRACT

An earplug for a hearing aid adapted for engagement with earpieces made of materials with a comparatively high hardness. The earplug comprises a resilient sleeve and a shell, the shell having an outer portion adapted to fit within a user's ear canal and a central bore, the central bore having a first abutment shoulder adapted for retaining the resilient sleeve inside the shell and a second abutment shoulder adapted for providing a stop for the resilient sleeve and for the earpiece. Hereby the resilient sleeve is able to combine relatively relaxed manufacturing tolerances with precise positioning of the earpiece inside the earplug.

4 Claims, 1 Drawing Sheet

EARPLUG WITH ENGAGEMENT MEANS

BACKGROUND OF THE INVENTION

1. Field of the Invention

The present invention relates to hearing aids. The invention, more specifically concerns a custom earplug for a hearing aid, adapted for engagement with an earpiece.

2. The Prior Art

WO-A1-2007006302 discloses a BTE hearing aid comprising a housing, an earpiece and a custom earplug. The word custom signifies that the earplug is adapted to fit the ear canal of an individual hearing aid user. The earpiece has a connector for cooperation with a socket of the custom earplug. The connector and the earpiece have means for snap fitting engagement and means for defining the mutual rotational orientation. The connector may comprise at least one locking means so that the connector can be smoothly positioned when pressed into place and so that a larger force is needed for pulling the connector out of the engagement. The connector may further comprise a guide that secures that the earpiece and the earplug are mounted in the right mutual position. The guide may be formed as a slit. The earplug may comprise a stop for positioning the connector in the earplug. In a preferred embodiment the stop is a shoulder preventing the connector from being pressed too far into the earplug.

The aim of this invention is to improve the design of such an earplug in order to allow the use of earpieces made of materials with a comparatively high hardness without requiring strict manufacturing tolerances. Hard materials may be advantageous with respect to e.g. higher transparency and enhanced bio-compatibility. However, snap fitting engagement means designed for use with two specimens made from materials of a relatively high hardness require strict manufacturing tolerances.

SUMMARY OF THE INVENTION

The invention provides an earplug for a hearing aid, adapted for engagement with an earpiece, comprising a resilient sleeve and a shell, the shell having an outer portion adapted to fit within a user's ear canal and a central bore, the central bore having a first abutment shoulder adapted for retaining the resilient sleeve inside the shell and a second abutment shoulder adapted for providing a stop for the resilient sleeve and for the earpiece.

Hereby the resilient sleeve is able to combine comparatively relaxed manufacturing tolerances with precise positioning of the earpiece inside the earplug. The second abutment shoulder ensures positioning of the sound emitting portion of the earpiece once inserted into the earplug. Additionally, this earplug design allows easy insertion and removal of the earpiece. The removal of the earpiece is accomplished using a simple translatory pull. It is a further advantage that the resilient sleeve once inserted in the shell will not easily separate, e.g. during transportation to, or handling at, the dispenser.

According to an embodiment the resilient sleeve is formed as a section of tube, which is cut into the appropriate size. In one embodiment the resilient sleeve is made in a polymer or plastic material with a shore A reading between 40 and 100. In another embodiment the shell is made of a photo acrylic, which is suitable for processing by a Stereo Lithography Apparatus. In yet another embodiment correct rotational positioning of the earpiece relative to the earplug is ensured by having a guide in the form of a keyway in the earplug and corresponding key parts on the earpiece.

BRIEF DESCRIPTION OF THE DRAWINGS

The invention is further explained in the following with reference to the schematic drawings of an embodiment of the invention. In the drawings.

DETAILED DESCRIPTION OF THE INVENTION

Figure 1:
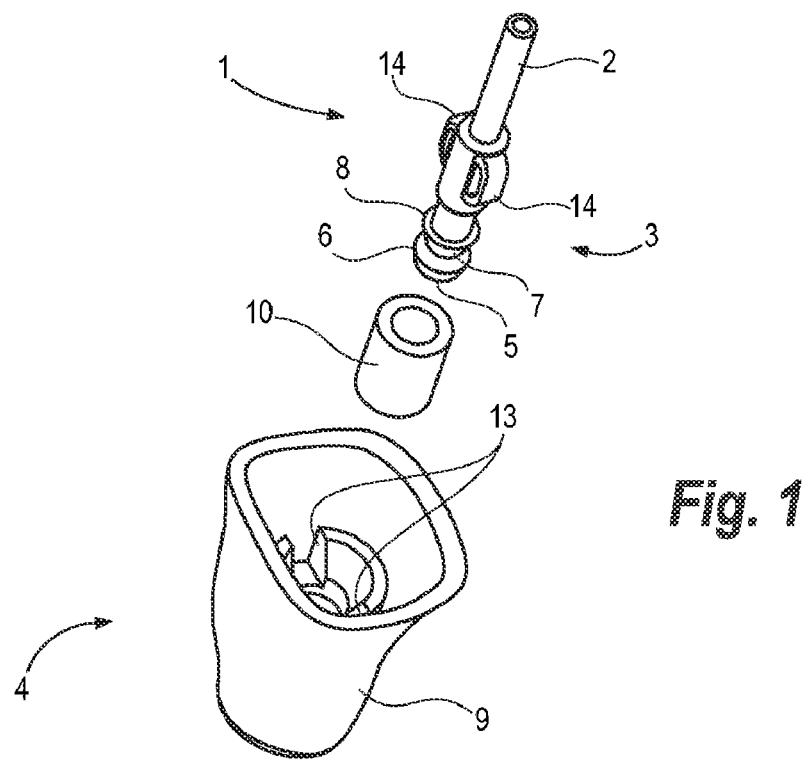
FIG. 1 is an exploded view of the earpiece and the earplug.
Figure 2:
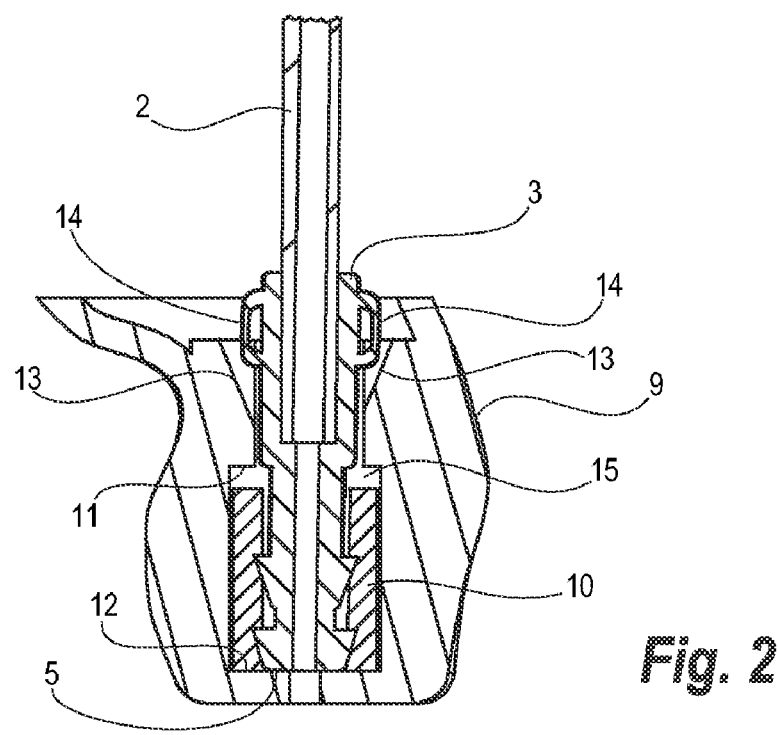
FIG. 2 shows a corresponding cross section of the earpiece and earplug when fully assembled.

The earpiece 1 comprises a sound tube 2 and a peg 3 adapted for connection of the sound tube to the earplug 4. The peg 3 comprises a distal end 5 adapted for being first inserted into the earplug 4, a proximal end adapted for connection with the sound tube 2, a first bead 6, an annular circumferential groove 7 and a second bead 8.

The earplug 4 comprises a shell 9 and a resilient sleeve 10. The shell 9 further comprises an outer portion adapted to fit within a user's ear canal and a central bore 15 with a first abutment shoulder 11 and a second abutment shoulder 12. The shell is made of a photo acrylic material, preferably by processing in an Stereo Litographic Apparatus. The resilient sleeve is a generally cylindrical body with an axial lumen made from a plastic material with a hardness corresponding to a Shore A reading of 40-100.

Additionally the shell 9 has a keyway 13, and the earpiece 1 has two key parts 14.

Precise and secure positioning of the sound emitting portion of the earpiece 1 inside the earplug 4 is accomplished by first inserting the resilient sleeve 10 into the central bore 15 past the first abutment shoulder 11 of the earplug 4 and subsequently inserting the earpiece peg 3 into the earplug 4 and into the lumen of the resilient sleeve 10, until the distal end 5 of the earpiece peg 3 touches the second abutment shoulder 12 of the earplug 4. Hereby the earpiece peg 3 expands the resilient sleeve 10 in such a way as to increase significantly the friction between both the earpiece peg 3 and the resilient sleeve 10 as well as between the resilient sleeve 10 and the central bore 15 of the shell 9 and thereby keeping the position of the earpiece fixed inside the earplug.

In order to keep the resilient sleeve 10 inside the earplug 4, before the earpiece peg 3 is inserted, the central bore 15 of the shell 9 has a first reduced portion, which forms a first abutment shoulder 11, that acts as a stop for the resilient sleeve 10, once the resilient sleeve 10 has been pressed past the said first abutment shoulder 11 and subsequently allowed to expand.

In order to ensure that the earpiece peg 3 is connected to the earplug 4 in the right rotational position, the keyway 13 in the shell 9 is adapted to accommodate the key parts 14 on the earpiece 1.

We claim:

1. An earplug for a hearing aid, adapted for engagement with an earpiece, comprising a resilient sleeve and a separate shell, the shell having an outer portion that fits within a user's ear canal and a central bore, the central bore having a first abutment shoulder that retains the resilient sleeve inside the shell and a second abutment shoulder that stops the resilient sleeve and the earpiece.

2. The earplug according to claim 1, wherein the resilient sleeve is made from a plastic material having a Shore A reading between 40 and 100.

3. The earplug according to claim 1, wherein the shell is made of a photo acrylic.

4. The earplug according to claim 1, wherein the shell is having a keyway that accommodates two key parts of the earpiece.

\* \* \* \* \*